(12) United States Patent
van Der Weegen

(10) Patent No.: US 6,258,024 B1
(45) Date of Patent: Jul. 10, 2001

(54) SPECULUM DEVICE

(75) Inventor: Clemens van Der Weegen, Strathfield (AU)

(73) Assignee: S.S.H. Medical Limited, New South Wales (AU)

( * ) Notice: Subject to any disclaimer, the term of this patent is extended or adjusted under 35 U.S.C. 154(b) by 0 days.

(21) Appl. No.: 09/297,534
(22) PCT Filed: Oct. 31, 1997
(86) PCT No.: PCT/AU97/00732
  § 371 Date: Jul. 2, 1999
  § 102(e) Date: Jul. 2, 1999
(87) PCT Pub. No.: WO98/19590
  PCT Pub. Date: May 14, 1998

(30) Foreign Application Priority Data

Nov. 1, 1996 (AU) .................................................. PO 3403

(51) Int. Cl.⁷ ....................................................... A61B 1/00
(52) U.S. Cl. .......................... 600/115; 600/116; 600/114; 600/208; 606/193; 606/192; 606/191; 604/97.01; 604/96.01
(58) Field of Search ..................................... 600/115, 114, 600/116, 207; 606/191, 192, 193; 604/96.01, 97.01

(56) References Cited

U.S. PATENT DOCUMENTS

| 5,104,377 | * | 4/1992 | Levine | 604/101 |
| 5,263,962 | * | 11/1993 | Johnson et al. | 606/192 |
| 5,368,598 | * | 11/1994 | Hasson | 606/119 |
| 5,624,399 | * | 4/1997 | Ackerman | 604/96 |
| 5,722,983 | * | 3/1998 | Van Der Weegen | 606/193 |
| 5,855,549 | * | 1/1999 | Newman | 600/135 |
| 5,921,917 | * | 7/1999 | Barthel et al. | 600/120 |

FOREIGN PATENT DOCUMENTS

PCT/AU94/00111  3/1994  (WO).

OTHER PUBLICATIONS

Derwent Publications Ltd., Abstract Accession No. 1 84–205473/33, SU A 1060–190 (Zaporo Health Department, Dec. 15, 1983.

* cited by examiner

Primary Examiner—Linda C. M. Dvorak
Assistant Examiner—Jocelyn Ram
(74) Attorney, Agent, or Firm—Paul & Paul

(57) ABSTRACT

A probe for a speculum for use in examining the interior of a body cavity. The probe comprised an elongated tubular member (1) having a first and second end and an expandable sealing element (2) encircling said tubular member at or near the first end (3). A means for admission of a fluid (50) is provided to the interior of said sealing element to effect expansion thereof. A removable closure means is adapted to engage the second end (30). A means for admission of a fluid into the bore of said tubular member is also provided (32). The closure means provides a line of sight and extending there through and along the bore of the tubular member.

19 Claims, 8 Drawing Sheets

SPECULUM DEVICE

TECHNICAL FIELD

This invention relates to dilating speculums, that is to say surgical instruments of various forms used for dilating body cavities and/or the orifices thereof so as to facilitate examinations of, or operations within, the interior of the cavity. In particular the present invention is directed towards a disposable probe for a dilating speculum.

BACKGROUND ART

Generally speaking, there are two types of speculums in common use, namely those that do not substantially dilate the body cavity and those that do.

Non-dilating speculums are relatively simple tubular devices, frequently made of transparent plastics material, frequently fitted with an eyepiece including a light source, which are inserted into the body cavity to enable it to be inspected. Sometimes that part of the speculum that enters the body cavity is a detachable, single use, disposable item.

Prior known dilating speculums have comprised a tubular array of two or more rigid, elongate leaves, frequently of arcuate cross section, and means to expand the array by bodily, generally radially outwardly, movement of the individual leaves.

It is usual, because of the need for strength, for dilating speculums to be made of metal. This has precluded the use of disposable, single use components in such speculums, rendering it necessary for dilating speculums to be throughly cleaned and sterilised after use.

Quite often it is desirable or necessary for the inspection to be performed on a conscious and alert patient, and almost invariably this causes discomfort at least, and in many instances considerable pain. This is particularly so when relatively simple dilating speculums comprising only two separable leaves are used.

Furthermore, the insertion of metallic objects into body orifices, and the cold sensation created thereby, is psychologically distressing to many patients. So much so that some women put themselves at risk by failing to have routine vaginal examinations as a check on possible cervical cancer, for example, so called pap smears, merely because of their repugnance to the use of prior known metallic dilating speculums.

Attempts to alleviate the unpleasantness associated with the use of simple prior known dilating speculums have resulted in speculums having more than two leaves. This reduces the pressure between the speculum and the surface of the dilated cavity, but introduces still further undesirable complexity into the mechanism with consequent high cost, and of course does nothing to alleviate the disadvantage of metallic speculums indicated above.

A dilating speculum which overcomes many of the disadvantages of the above mentioned prior known dilating speculums is disclosed in International Patent Application No. PCT/AU94/00111 in the name of Clemens Van der Weegen.

However, a problem associated with such a speculum is that it requires considerable assembly of parts. Such assembly increases the risk of contaminating sterile components of the speculum, and also increases the time to set up the speculum for use.

An object of the invention is to provide a probe for a dilating speculum which is simple to assemble and of a single use disposable type and facilitates inspection of a body cavity.

SUMMARY OF INVENTION

In one aspect, the present invention consists in a probe for a speculum for use in examining the interior of a body cavity, said probe comprising an elongate tubular member having a first end and a second end, an expandable sealing element encircling said tubular member at or near said first end, means for admission of a fluid to the interior of said sealing element to effect expansion thereof, a removable closure means for said second end, and means for admission of a fluid into the bore of said tubular member, characterised in that said closure means provides a line of sight extending through the closure means and along the bore of the tubular member.

Preferably said closure means forms part of an eye piece, hand piece or other extension device.

Preferably said removable closure means comprises a sealable entry port for a surgical implement.

Preferably the expandable sealing element is a substantially annular bladder, for example an element akin to a miniature inner tube for a pneumatic tyre, encircling the tubular member. The annular bladder is preferably of an elastomeric material such as latex or "silicone rubber" which is stretchably fitted onto the tubular member.

Preferably in one embodiment the annular bladder is secured to the tubular member by an elastomeric tie means.

Preferably in a second embodiment the annular bladder is secured to the tubular member by a string tie means.

Preferably in a third embodiment the annular bladder is secured to the tubular member by an adhesive means.

Preferably the means for admission of fluid to the interior of said sealing element comprises a duct extending from the interior of the sealing element to a fluid connection means. The fluid connection means is adapted to connect to a supply tube or the like extending to a remote air or other gas supply means such as a manually operated dilation bulb, thereby allowing for the annular bladder to be inflated. Alternatively, the annular bladder could be expandable by introducing fluid therein, such as water, from a suitable fluid supply.

Preferably the material of the tubular member is capable of transmitting light and may be of a moulded colourless transparent plastic such as acrylic or the like.

Preferably said second end of said tubular member is adapted to detachably secure to a re-usable hand piece. The hand piece may be a conventional unit combining a conventional light source, or a component thereof. The conventional unit or component thereof preferably has a spigot like member to which the second end of the probe detachably secures.

Alternatively, the hand piece may be fixed to the probe for disposal therewith.

The tubular member may have one or more faces in a region adjacent the spigot like member when connected thereto, which are preferably perpendicular to the direction of the light source projecting through or from the spigot like member. The faces are preferably polished to facilitate transmission of the light.

Preferably the means for admission of a fluid into the bore of said tubular member is integral with the removable closure means.

Preferably the means for admission of fluid into the bore of said tubular member comprises a gas connection means opening at one end into said bore and adapted at its other end for connection to the same remote air or other gas supply means as that connected to said expandable sealing element.

In one embodiment the removable closure means has a sleeve portion which sealingly engages with the internal bore surface of said tubular member.

In a further embodiment the removable closure means has a sleeve portion which sealingly engages with the external surface of said tubular member.

BRIEF DESCRIPTION OF THE DRAWING

By way of example, embodiments of the above described invention are described in more detail hereinafter with reference to the accompanying drawings.

MODE OF CARRYING OUT INVENTION

Figure 1:
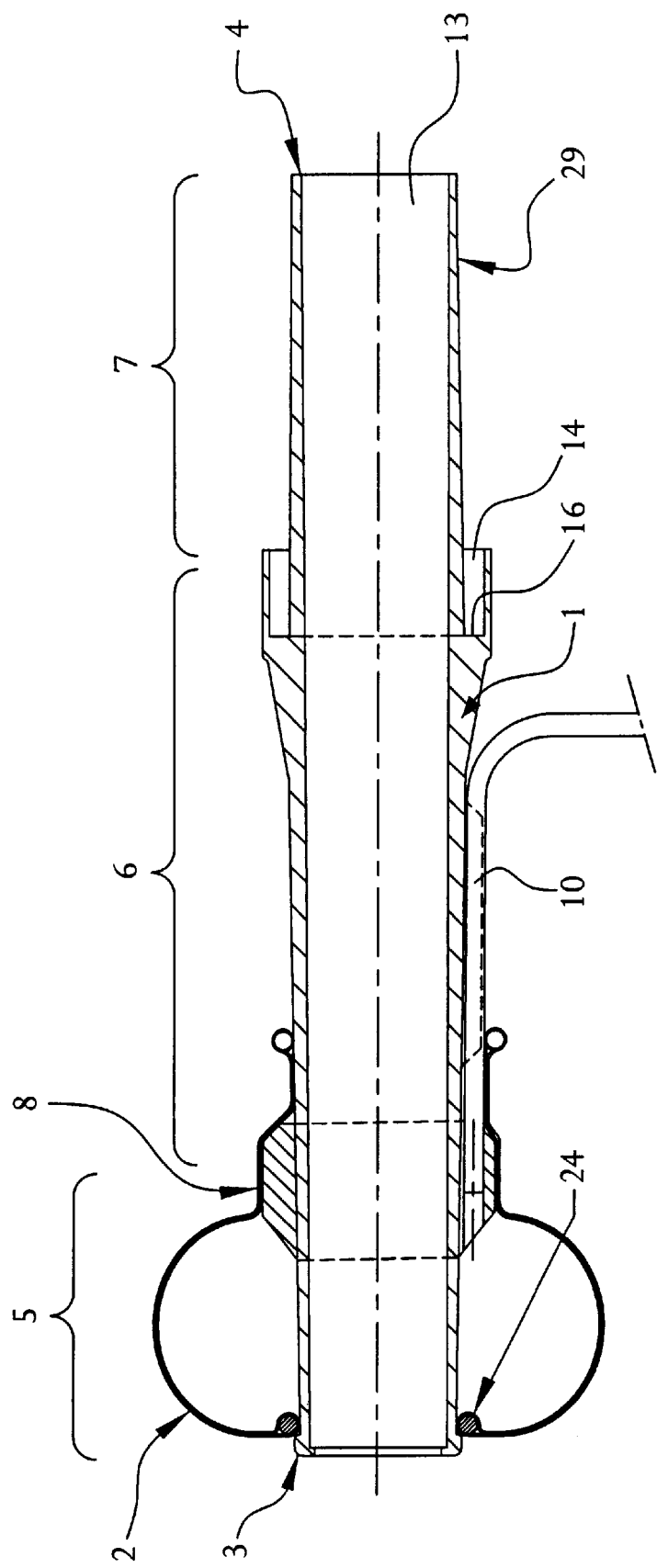
FIG. 1 is a longitudinal sectional view of a probe for a dilating speculum in accordance with a first embodiment of the present invention with the annular bladder in an inflated configuration and without its removable closure means fitted.
Figure 2:
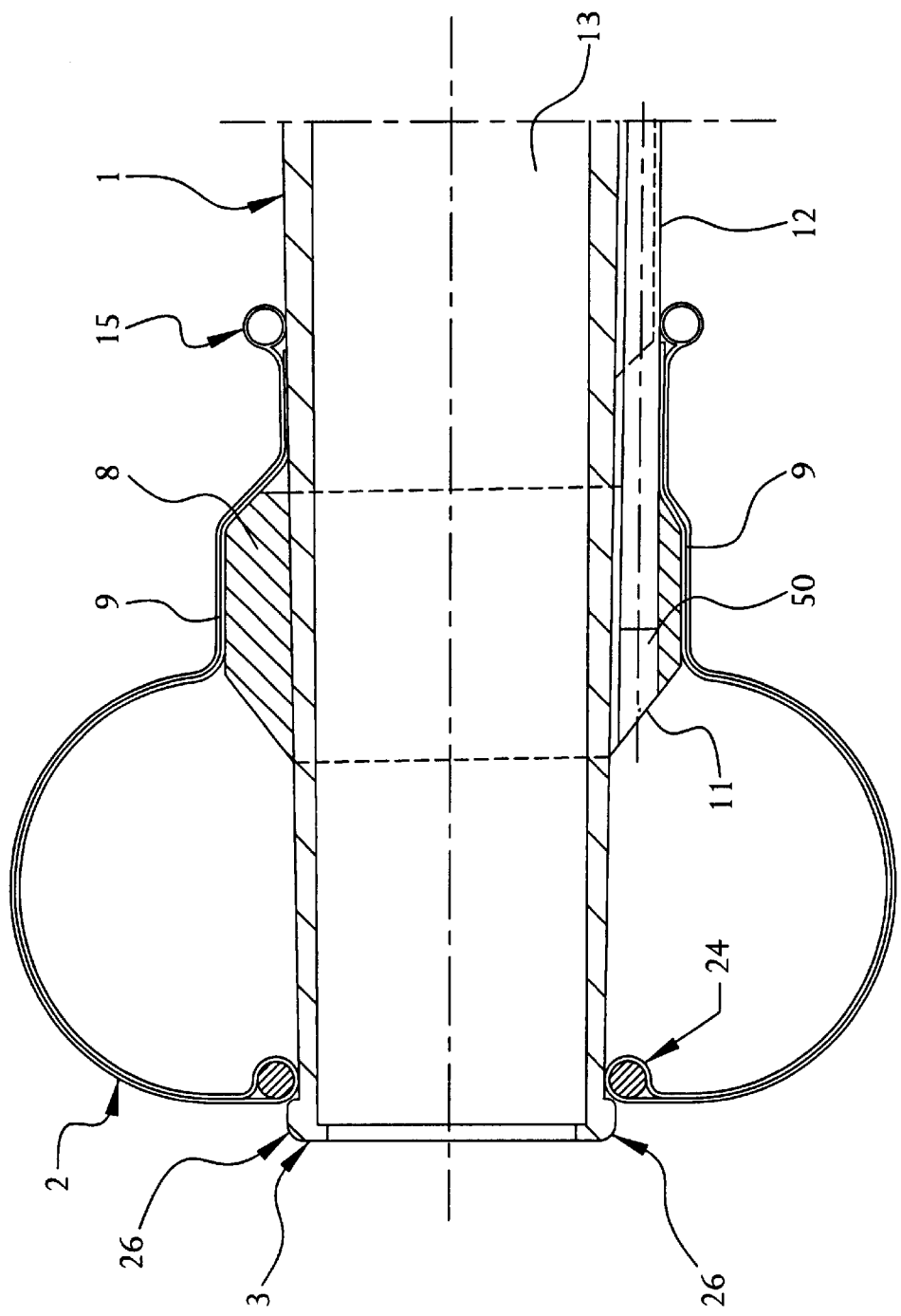
FIG. 2 is an enlarged sectional view of bladder end of the probe shown in FIG. 1.
Figure 3:
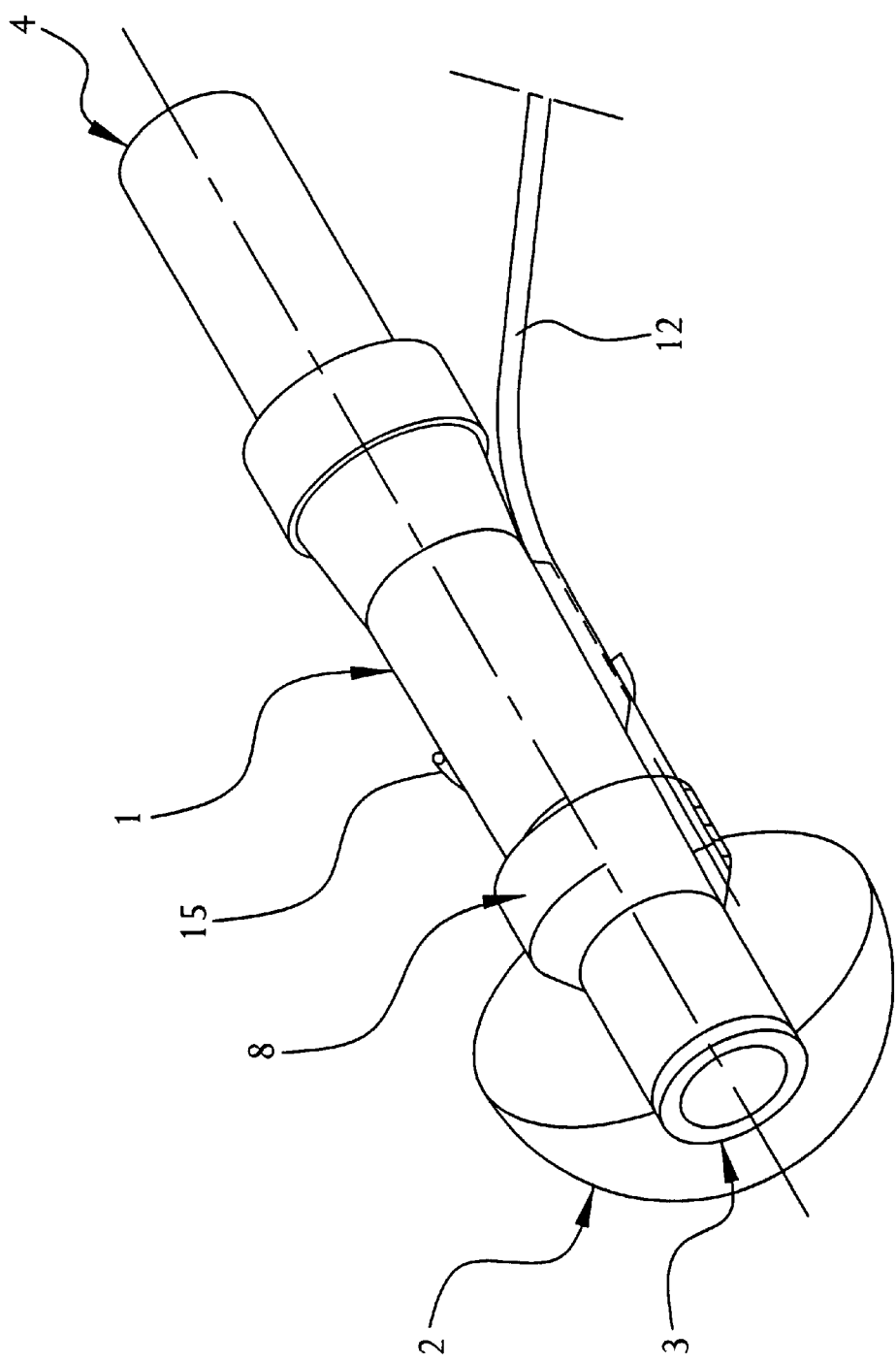
FIG. 3 is a perspective schematic view of the probe of FIG. 1 with a portion of the inflated bladder cut away.
Figure 4:
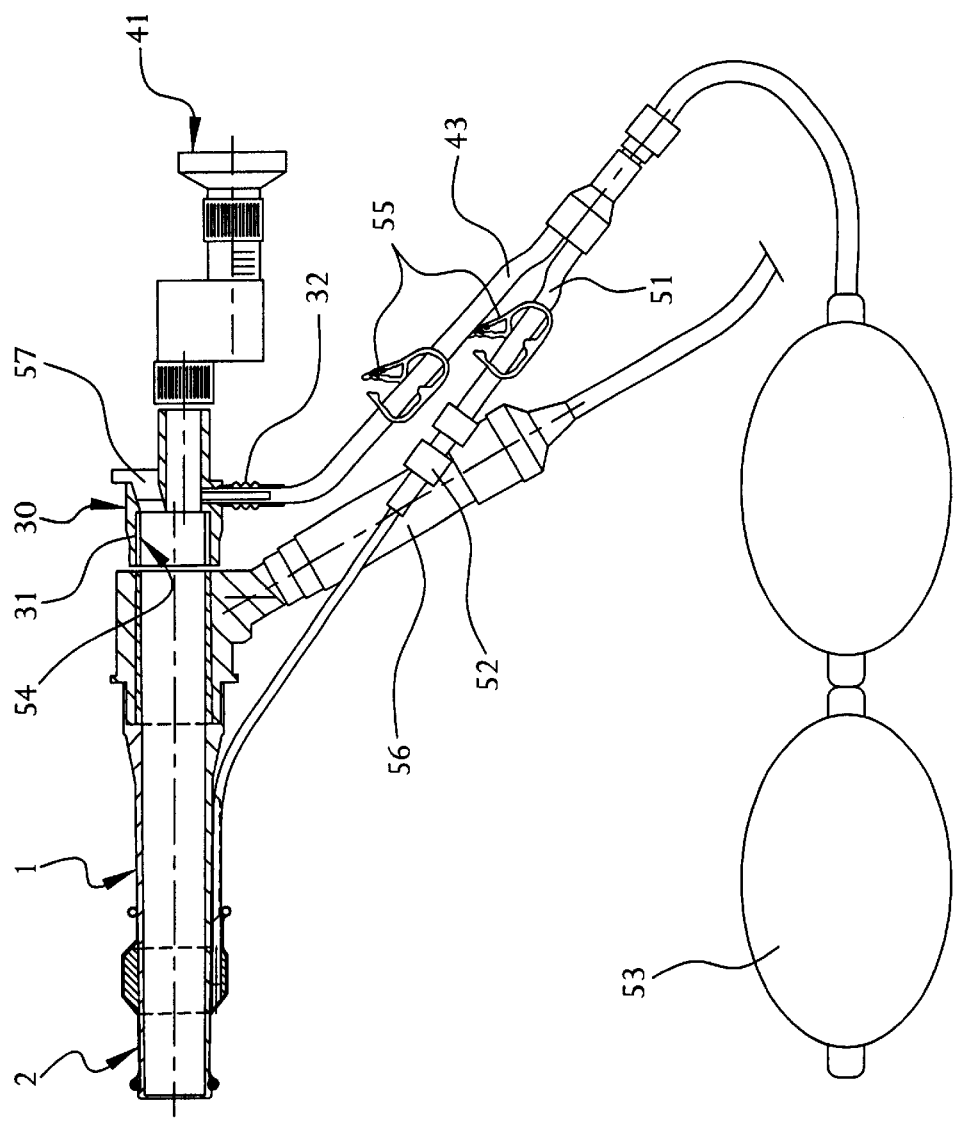
FIG. 4 is a longitudinal cross-sectional view of the probe of FIG. 1 with the annular bladder deflated, a hand piece fitted thereto and a removable closure means fitted.

FIGS. 1 to 4 depict a first embodiment of a probe for a speculum intended for use in the examination of the vagina. The probe comprises an elongate tubular member 1 having an elastomeric annular bladder 2 (shown in an inflated configuration in FIGS. 1 to 3) encircling it near its end 3. The other end 4 of tubular member 1 is adapted to detachably engage a hand piece 56 or component thereof typically comprising a handle with light source.

Tubular member 1 is a colourless transparent plastic moulding which may for example be of acrylic. For ease of reference tubular member 1 can be described as having three portions, a body entry portion 5, a middle portion 6 and an attachment portion 7.

A ring member 8 is fitted to tubular member 1 by means of a morse taper and spans body entry portion 5 and middle portion 6. The annular bladder 2 is a sleeve made of elastomeric material such as latex or "silicone rubber", a portion of which is stretchably fitted onto the tubular member 1 over its body entry portion 5 and ring member 8. A piece of adhesive tape 9 is secured tightly over that part of the elastomeric sleeve which surrounds the ring member 8 thereby sealing the sleeve against the ring member 8, see FIG. 2. An elastomeric tie means (rubber band) 24, secures and seals the sleeve near the end 3 of the tubular member. The sleeve material is doubled back aver itself and the tubular member, including the ring member 8, and the doubled back sleeve is held in place by a bead 15 integrally formed on the sleeve. The doubled back sleeve thereby forms annular bladder 2. The bead 15 is similar to the well known beads formed at the open end of elastomeric products such as party balloons, condoms and surgical gloves.

A bore 50, runs longitudinally through the wall of ring member 8 and is aligned with a groove 10 integrally formed on the middle portion 6 of tubular member 1. Bore 50 has one of its ends terminating at location 11 within annular bladder 2 and is adapted to house a gas duct such as a first air tube 12. During manufacture air tube 12 can be snap engaged into groove 10 and/or adhesively fixed therein. The end of the air tube 12 terminates within bore 50 allowing for pneumatic communication between the interior of bladder 2 and the other end of air tube 12 which is connected to a flexible tube 51 having an air supply nipple (or connector) 52 at its free end. The air supply nipple 52 is adapted to detachably connect to a manually operated dilation bulb 53 or other air supply means, which allows for air to be pumped into bladder 2.

A closure means, in the form of a cap 30, having an eye piece 41 and a sleeve portion 31 is adapted to sealingly engage over free end 4 of tubular member 1. A bore surface 54 of sleeve portion 31 contacts the outer surface 29 of tubular member 1 when cap 30 is in engagement therewith. Cap 30 has an opening 32 adapted to be connected to one end of a flexible tube 43, the other end of which may be connected to the same dilation bulb 53 or other air supply means which is connected to the flexible tube 51. Manually operable spring clips 55 associated with the dilation bulb 53 may be selectively squeezed to close the flexible tubes 51 and 43. Cap 30 also has a sealable entry port 57 for insertion of a surgical implement through cap 30 and into the probe. When a surgical implement is not being used in conjunction with the probe, the port 57 is sealed by a plug (not shown).

Middle portion 6 is larger in outside diameter and thicker in wall section than attachment portion 7 and body entry portion 5. Attachment portion 7 which extends from middle portion 6, has a wall section thinner than both the other portions, and at free end 4 is tapered. Annular recess 14 is located in grip portion 6 adjacent to where attachment portion 7 extends therefrom. Attachment portion 7 is adapted to be inserted into the bore of a spigot which forms part of re-usable hand piece 56, typically comprising a light source and handle as earlier described. Annular recess 14 is sized so that the free ends of the hand piece spigot can seat therein when attachment portion 7 is inserted into the spigot. A rib, projection or some other detent means (not shown) may exist in annular recess 14 to assist in holding tubular member 1 to the hand piece. Face 16 within recess 14 is preferably polished and the corners adjacent to the face 16 are square. This is to ensure that in use, the light emitted from the hand piece 56 through the free end of the spigot, is efficiently transmitted through the material of the tubular member 1.

The rounded circumferential corner 26 of free end 3 should be polished to ensure that it is smooth as possible to facilitate insertion into the vagina.

The assembly of the above described probe may be effected under sterile conditions in a factory or the like. Moulded tubular member 1 requires the attachment of the bladder 2, and the air tube 51 and air nipple 52.

In use the probe may be supplied in a sterile package for use by a medical practitioner at time of inspection. The speculum may then be set up for use by attaching the probe to the earlier described reusable hand piece 56. The procedure requires attachment portion 7 of the probe to be inserted into the spigot forming part of the hand piece 56. The manually operated dilation bulb 53 can then be attached to the first and second flexible tubes. During attachment the practitioner can hold the probe around grip portion 6 of tubular member 1.

In a typical embodiment the probe, once fitted to the hand piece 56 extends approximately 120 mm–200 mm, depending on the length of the probe thereby providing sufficient distance between the sterile body entry portion 5 of the probe and any part of the hand piece 56 which may be unsterile.

Once set up, the assembled speculum may be inserted into the vagina with bladder 2 in a deflated configuration. It should be noted that only a part of body entry portion 5 of tubular member 1 is inserted into the vagina sufficient to locate the bladder 2 within or beyond the opening of the vagina. The bladder is then inflated with air by means of the manually operated dilation bulb 53, such that the bladder 2 expands and seals with the vaginal opening.

Cap 30 is then seated on and seals free end 4 of tubular member 1. Air is then pumped through tubular member 1 to expand the inner cavity of the vagina, thereby permitting the user to inspect the vagina through eye piece 41 and locate where necessary the position of the cervix. The inspection of the inner cavity of the vagina is possible, as the cap 30 which incorporates eyepiece 41 provides a line of sight extending there through and along the bore 13 of the tubular member 1. In cases where a sample from the cervix is to be taken, the user once having located the cervix, may press free end 3 of tubular member 1 against the cervix, then remove cap 30 from free end 4. A sample may then be obtained by inserting a spatula through tubular member 1 and scraping off the necessary cellular material.

The bore 13 of the probe is of sufficient diameter to allow for biology forceps, suction tubes and other equipment to be passed therethrough during inspection and/or surgical procedures.

In practice when the examination is complete the air is exhausted from the bladder 2 and the probe removed from the vagina. The probe can then be removed from the hand piece 56 and disposed of. Thus the illustrated probe is a single use item and is discarded in total. Whilst the embodiment of the present invention can be used with a liner, it should be noted that as it is disposable it may also be utilised as is, without a liner being fitted to the bore of the probe.

It is preferable that when the attachment portion 7 is inserted into the bore of the spigot of hand piece 56 and detachably secured thereto, free end 4 projects beyond the opposite end of the bore of the spigot. This is to ensure that in use where tissue and body fluids may be extracted through bore 13 of tubular member 1, the risk of contaminating the hand piece 66 is minimised.

Figure 5:
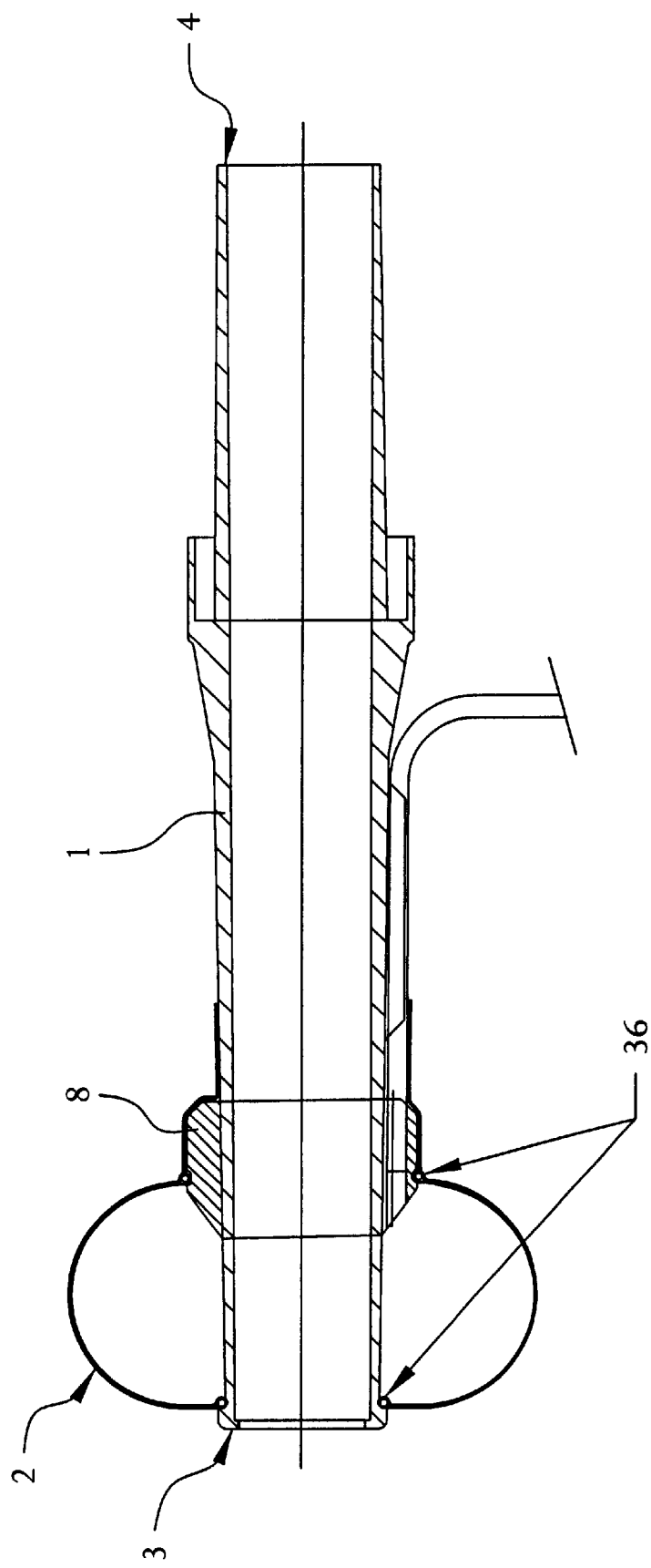
FIG. 5 is a longitudinal cross-sectional view of a probe for a dilating speculum in accordance with a second embodiment of the present invention with the annular bladder in an inflated configuration and without its removable closure means fitted.
Figure 6:
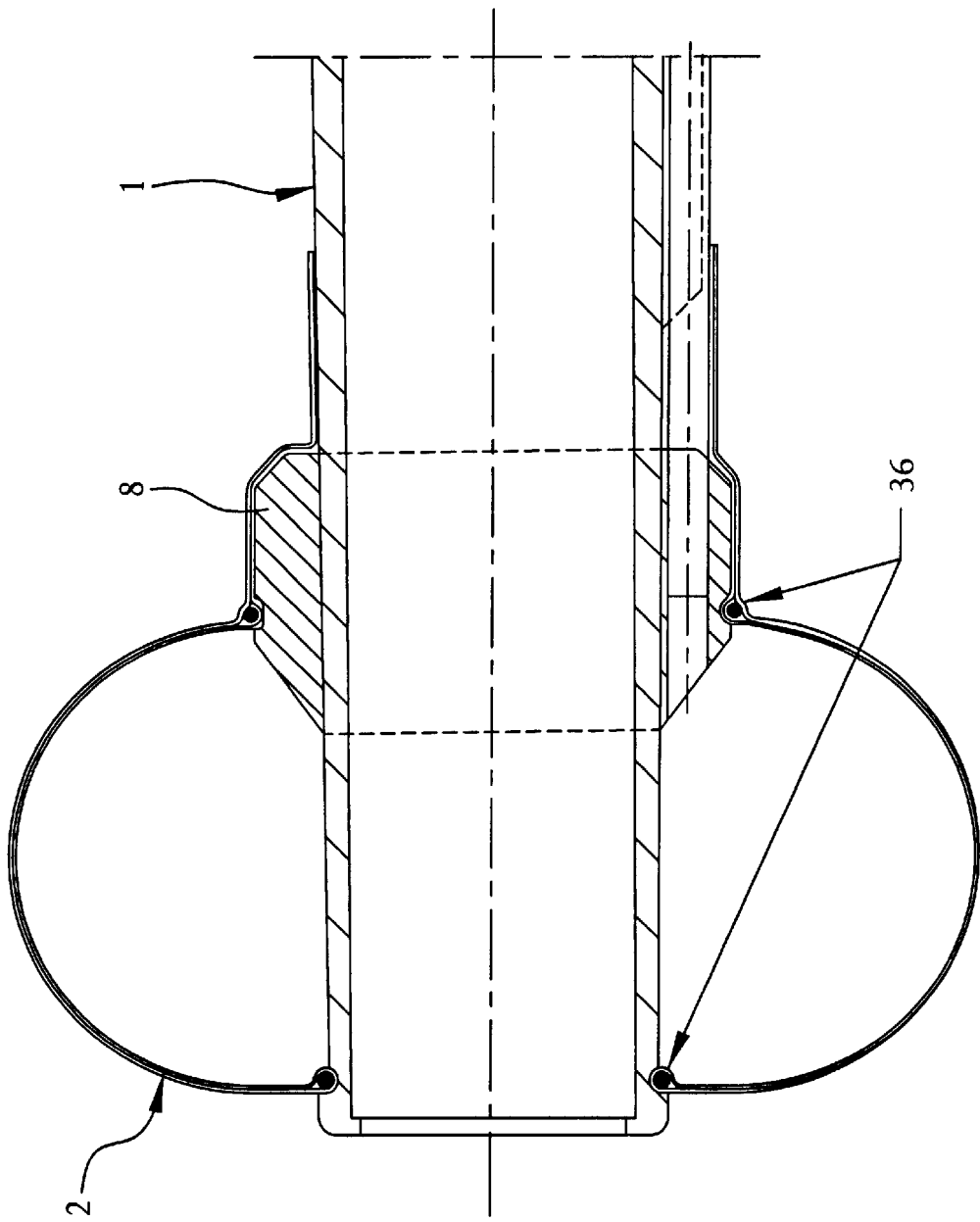
FIG. 6 is an enlarged sectional view of the end of the bladder end of the probe shown in FIG. 5.

It should also be noted that in other embodiments the configuration and shape of the components may differ without altering the scope of the invention. For instance, the annular bladder may be similar to that described earlier, but utilise a different means of securing and sealing the stretchably fitted sleeve which forms the annular bladder 2. For instance in a second embodiment of the probe as shown in FIGS. 5 and 6, twine ties 36 may be used instead of an elastomeric tie means 24 of the first embodiment. In such second embodiment the sleeve material which forms the annular bladder is doubled back over itself and the tubular member, including the ring member 8 in a like manner to the earlier described embodiment.

Figure 7:
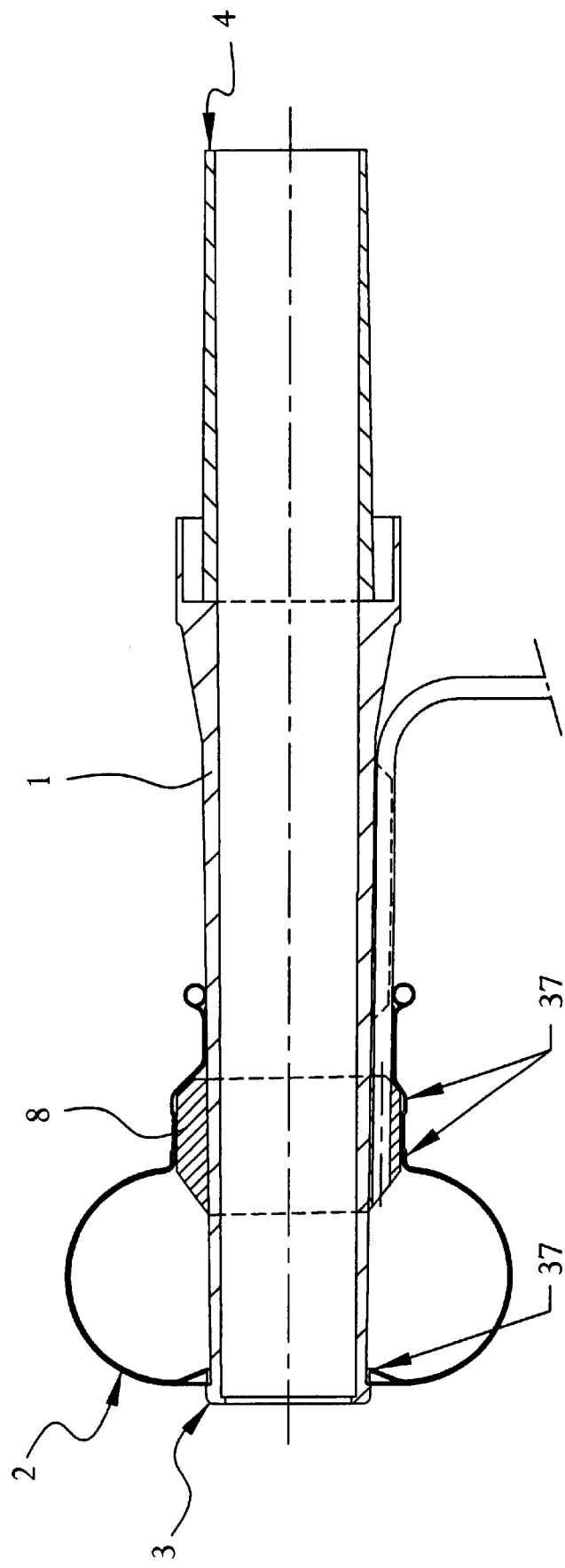
FIG. 7 is a diagrammatic longitudinal sectional view of a probe for a dilating speculum in accordance with a third embodiment of the present invention with the annular bladder in an inflated configuration and without its removable closure means fitted.
Figure 8:
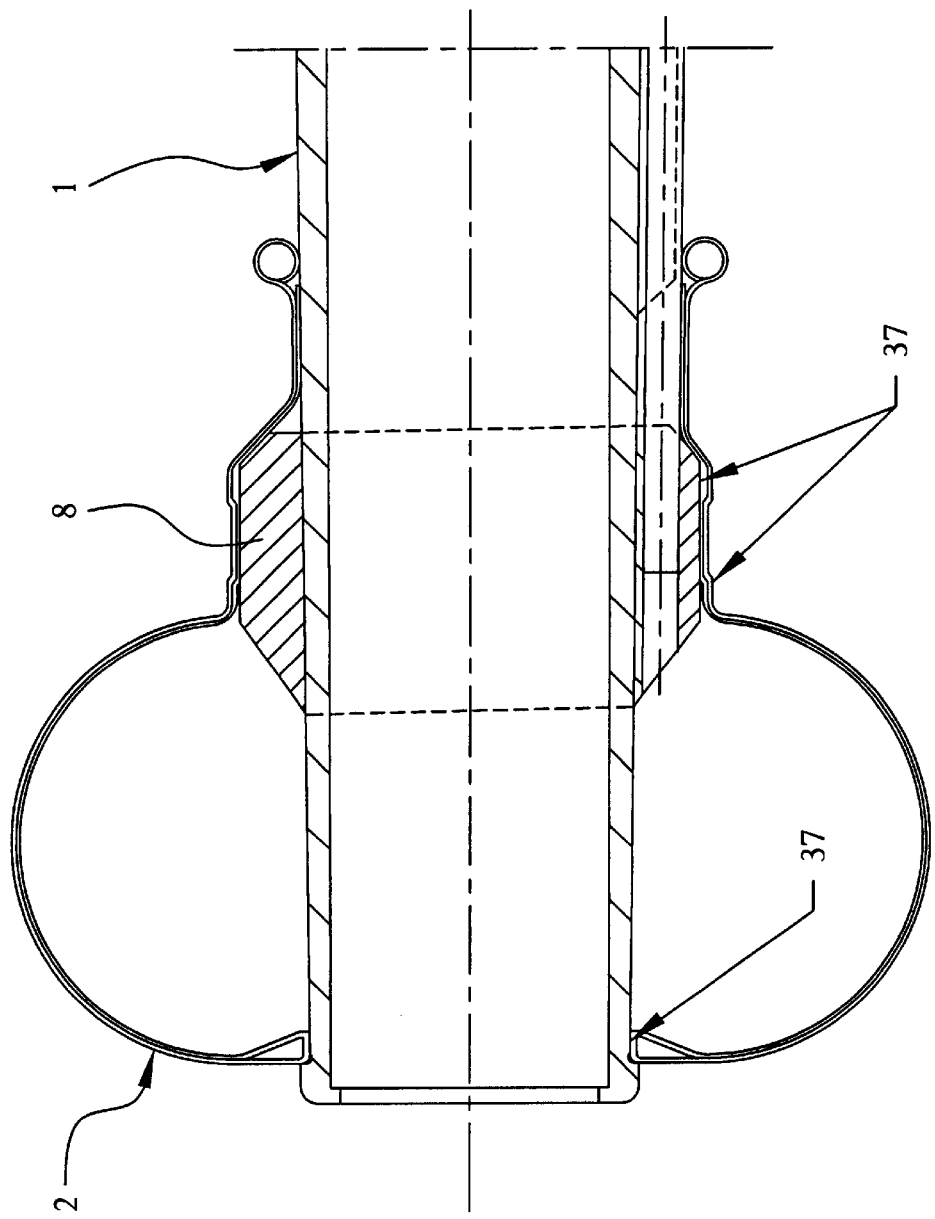
FIG. 8 is an enlarged sectional view of the end of the bladder end of the probe shown in FIG. 7.

In a third embodiment of the probe as shown in FIGS. 7 and 8, where the annular bladder is made of a material such as latex, adhesive (glue) joints 37 may be used instead of the elastomeric tie means 9 or twine ties 36 of the earlier embodiments. In such a third embodiment the sleeve material which forms the annular bladder 2 is also doubled back over itself and the tubular member, including the ring member 8 in a like manner to the earlier described embodiment.

In the earlier described embodiment, tubular member 1, which is moulded from plastic such as acrylic, is substantially rigid. However, in further not shown embodiments tubular member 1 may be manufactured from a plastic material which has greater flexibility whilst still being able to be inserted into a body cavity.

In another not shown embodiment the cap 30 may alternatively have a sleeve portion which slidably engages internally of tubular member 1.

In a further not shown embodiment the hand piece 56 and cap 30 may form part of single device attachable to attachment portion 7 of the tubular member 1. The cap 30 being removable or openable from the hand piece thereby permitting access to the bore 13 of tubular member and vagina through free end 4.

Although described above primarily with reference to examination of the vagina, it will be appreciated that probes for speculums according to the invention, but probably modified in respect of the size and shape of their various components to suit the body cavity concerned, may be used quite generally for internal examination of other body cavities, for example the lower bowel, or, for veterinary use, the body cavities of animals.

What is claimed is:

1. A disposable probe for a speculum for use in examining the interior of a body cavity, said probe comprising an elongate, rigid tubular member having a see-through bore extending between a first end and a second end of the tubular member, an expandable sealing element encircling said tubular member at or near said first end, means for admission of a fluid to the interior of said sealing element to effect expansion thereof, a removable closure means for said second end, and means for admission of a transparent fluid into said bore, characterized in that said closure means permits direct vision through said bore.

2. A probe for a speculum as claimed in claim 1 wherein said closure means forms part of an eye piece, hand piece or other extension device.

3. A probe for a speculum as claimed in claim 1 wherein the removable closure means comprises a sealable entry port for a surgical implement.

4. A probe for a speculum as claimed in claim 1 wherein said expandable sealing element is a substantially annular bladder.

5. A probe for a speculum as claimed in claim 4 wherein the annular bladder is an elastomeric material stretchably fitted onto the tubular member.

6. A probe for a speculum as claimed in claim 5 wherein the annular bladder is secured to the tubular member by an elastomeric tie means.

7. A probe for a speculum as claimed in claim 5 wherein the annular bladder is secured to the tubular member by a string tie means.

8. A probe for a speculum as claimed in claim 5 wherein the annular bladder is secured to the tubular member by an adhesive means.

9. A probe for a speculum as claimed in claim 1, wherein said means for admission of fluid to the interior of said sealing element is an annular bladder comprising a duct extending from the interior of the sealing element to a fluid connection means.

10. A probe for a speculum as claimed in claim 9 wherein said fluid connection means are adapted to connect to a supply tube extending to a remote air supply means thereby allowing for the annular bladder to be inflated.

11. A probe for a speculum as claimed in claim 1 wherein said tubular member is made of material that is capable of transmitting light.

12. A probe for a speculum as claimed in claim 11 wherein said tubular member is of a moulded colourless transparent plastic.

13. A combination of a probe for a speculum as claimed in claim 1 and a re-usable hand piece, wherein said tubular member is detachably secured to the hand piece.

14. A combination of a probe for a speculum as claimed in claim 13 and a re-usable hand piece, to which the probe is detachably secured, wherein the hand piece includes a light source to project light from the hand piece into the material of the tubular member.

15. A combination as claimed in claim 14, wherein said tubular member and said hand piece have respectively juxtaposed faces through which the light is projected, and which are perpendicular to the direction of the light passing through them.

16. A combination as claimed in claim 15 wherein said faces are polished to facilitate the transmission of the light from the hand piece to the tubular member.

17. A probe for a speculum as claimed in claim 1, wherein said means for admission of a fluid into the bore of said tubular member is integral with the removable closure means.

18. A probe for a speculum as claimed in claim 1, wherein said means for admission of fluid into the bore of said tubular member comprises an air connection means opening at one end into said bore.

19. A probe for a speculum as claimed in claim 1, wherein said removable closure means has a sleeve portion which sealingly engages with the external surface of said tubular member.

* * * * *